United States Patent [19]
Bancroft

[11] Patent Number: 6,149,596
[45] Date of Patent: Nov. 21, 2000

[54] ULTRASONIC CATHETER APPARATUS AND METHOD

[76] Inventor: Michael R. Bancroft, 27 Somersworth Cir., Salinas, Calif. 93906

[21] Appl. No.: 09/187,237

[22] Filed: Nov. 5, 1998

[51] Int. Cl.[7] .................................................. A61B 8/00
[52] U.S. Cl. ........................................... 600/439; 600/437
[58] Field of Search .................................... 606/159, 128, 606/7, 194, 144; 600/128, 439, 438, 437; 604/22

[56] References Cited

U.S. PATENT DOCUMENTS

| | | | |
|---|---|---|---|
| 4,545,390 | 10/1985 | Leary | 128/772 |
| 4,582,067 | 4/1986 | Silverstein et al. | 128/663 |
| 4,744,366 | 5/1988 | Jang | 606/194 |
| 4,832,023 | 5/1989 | Murphy-Chutorian et al. | 606/128 |
| 4,870,953 | 10/1989 | DonMicheal et al. | 606/7 |
| 5,000,185 | 3/1991 | Yock | 128/662.03 |
| 5,002,059 | 3/1991 | Crowley et al. | 128/662.06 |
| 5,109,859 | 5/1992 | Jenkins | 128/662.03 |
| 5,190,046 | 3/1993 | Shturman | 128/662.06 |
| 5,318,014 | 6/1994 | Carter | 606/128 |
| 5,320,106 | 6/1994 | Tanaka | 128/662.06 |
| 5,354,220 | 10/1994 | Ganguly et al. | 439/675 |
| 5,505,088 | 4/1996 | Chanraratna et al. | 73/623 |
| 5,513,639 | 5/1996 | Satomi et al. | 128/660.1 |
| 5,546,947 | 8/1996 | Yagami et al. | 128/662.06 |
| 5,570,693 | 11/1996 | Jang et al. | 128/662.06 |

*Primary Examiner*—Marvin M. Lateef
*Assistant Examiner*—Maulin Patel

[57] ABSTRACT

The ultrasonic cardiac catheter apparatus comprises a catheter member, an ultrasound generator source and means containing liquid chemicals that will aid in carrying the high frequency sound waves, or will aid in identifying or dissolving the blockage. The catheter member is adapted having a suitable length and having, at one end, a central port or coupling to the ultrasonic sound generator, and for coupling to selected liquid chemical sources, such as sterile normal saline, dyes or clot busting chemicals that act, respectively, as sound carriers means, catheter inflating means, or that are used to help identify the location of a blockage, or help dissolve blockages. The catheter member is used in conjunction with an introducer and sheath means. The catheter member may be made of flexible tubular material that facilitates balloon action, or may be made of ceramic fibers whose structure facilitates transmission of sound impulses to the location to be cleared. The ultrasound generator is a commercially available medical equipment unit adapted to couple to the catheter's central port to deliver the sound impulses. A first ultrasonic signal is used to measure the density of blockage. A second ultrasonic signal is generated at a frequency resonant with the measured density of the blockage to emulsify the blockage.

16 Claims, 6 Drawing Sheets

ULTRASONIC CATHETER APPARATUS AND METHOD

FIELD OF THE INVENTION

The present invention relates to catheter apparatus and methods of use in the cardiovascular field. More particularly, the present invention relates to ultrasonic catheter apparatus and methods of use in the cardiovascular field. Even more particularly, the present invention relates to ultrasonic catheter apparatus and methods of use in the cardiovascular field wherein cardiac vessels are cleared of plaque and other obstructions by the use of ultrasound.

BACKGROUND OF THE INVENTION

Catheter apparatus are used for many purposes, including administering intravenous fluids and drugs, and are especially useful in the cardiovascular field. Ultrasonic cardiac catheter apparatus have been patented as is evident from prior art patents. Exemplary of patents concerning ultrasonic cardiac catheter apparatus are:

| U.S. Pat. No. | Inventor | Date of Issue |
| --- | --- | --- |
| 4,545,390 | James J. Leary | Oct. 08, 1985 |
| 4,582,067 | Fred E. Silverstein, et al. | Apr. 15, 1986 |
| 5,000,185 | Paul G. Yock | Mar. 19, 1991 |
| 5,002,059 | Robert J. Crowley, et al. | Mar. 26, 1991 |
| 5,109,859 | Ronald D. Jenkins | May 05, 1992 |
| 5,354,220 | Dipankar Ganguly, et al. | Oct. 11, 1994 |
| 5,505,088 | P. Anthony N. Chandraratna, et al. | Apr. 09, 1996 |
| 5,513,639 | Gengi Satomi, et al. | May 07, 1996 |
| 5,546,947 | Hiroyuki Yagami, et al. | Aug. 20, 1996 |
| 5,570,693 | Yue-Teh Jang, et al. | Nov. 05, 1996 |

A brief description of the listed prior art patents follows: U.S. Pat. No. 4,582,067 teaches a catheter apparatus and method including an ultrasonic probe for introducing an ultrasonic field into arteries. The method includes monitoring a Doppler signal to obtain blood flow data. U.S. Pat. No. 4,545,390 teaches a guide wire and dilation catheter combination for use in coronary angioplasty techniques. The apparatus includes lumen means for delivering liquids and delivering air to inflate a balloon. The external end includes a Y-fitting for coupling to liquid or air sources. U.S. Pat. No. 5,000,185 teaches, in one embodiment, a catheter apparatus comprising a tubular element having at least four (4) lumens and an ultrasonic transducer. The catheter is provided in various sizes. The schematic of FIG. 6 provides an overview of the system. The apparatus uses piezoelectric crystal oscillators and disclose the use of other means. A cutter device 29 is employed in the apparatus. U.S. Pat. No. 5,002,059 teaches an ultrasound catheter device comprising a catheter sheath, an elastomeric septum which contains ultrasonic transmission fluid such as sterile water or saline solution. U.S. Pat. No. 5,109,859 teaches a laser angioplasty catheter for use in removing atherosclerotic plaque from coronary arteries. The device includes an ultrasound transducer, a balloon and a fiber optic waveguide for receiving laser energy. U.S. Pat. No. 5,190,046 teaches an ultrasound imaging balloon catheter apparatus including an ultrasound transducer, catheter and balloon arrangement. U.S. Pat. No. 5,320,106 teaches an intracavitary diagnosing apparatus including a transducer and an ultrasonic mirror for directing ultrasound into an organ. U.S. Pat. No. 5,354,220 teaches an electrical coupler for coupling an ultrasonic transducer to a catheter. The catheter coupler interfaces with a control and processing system, as shown in FIG. 7. U.S. Pat. No. 5,505,088 teaches an ultrasound microscope means including an ultrasound transducer means for transmitting an receiving ultrasound for imaging living tissues. U.S. Pat. No. 5,546,947 teaches an ultrasonic endoprobe having a metal tube made from a superelastic material. The metal tube encloses an ultrasonic transducer. The apparatus has utility in examination of hollow organs or parts of a living body. U.S. Pat. No. 5,513,639 teaches an ultrasonic diagnostic probe for use in imaging body cavities. The probe includes an inflatable balloon member having space for carrying an array of piezoelectric elements. U.S. Pat. No. 5,570,693 teaches an intravascular ultrasound imaging apparatus. The apparatus comprises a catheter body and a transducer that ultrasonically scans the vessel to create an image. The apparatus also includes a cutter for performing atherectomy.

The foregoing patents primarily teach the use of ultrasonic devices and method for imaging of blockages in vessels, but do not teach, suggest or motivate apparatus and method that uses sound waves selected to resonate at selected required sound frequencies to liquidize the solid obstruction in a cardiac vessel.

Accordingly, it is a primary object of the present invention to provide an ultrasonic cardiac catheter apparatus and method that uses sound waves selected to resonate at selected required sound frequencies to liquidize the solid obstruction in a cardiac vessel.

A related object of the present invention to provide an ultrasonic cardiac catheter apparatus and method that combines the imaging attributes of the ultrasonic catheter apparatus in combination with attributes that uses sound waves selected to resonate at selected required sound frequencies to liquidize the solid obstruction in a cardiac vessel.

BRIEF SUMMARY OF THE INVENTION

Accordingly, the foregoing objects are accomplished by an ultrasonic cardiac catheter apparatus comprising a catheter member, an ultrasound generator source, and means containing liquid chemicals that will aid in carrying the high frequency sound waves, or will aid in identifying or dissolving the blockage. The catheter member is adapted having a suitable length and having, at one end, a central port means for coupling to the ultrasonic sound generator and light source means, and for coupling to selected liquid chemical sources, such as sterile normal saline, dyes or clot busting chemicals that act, respectively, as sound carriers means, catheter inflating means, or that are used to help identify the location of a blockage, or help dissolve blockages. The catheter member is used in conjunction with an introducer and sheath means, as well as a light source to locate and reach a target vascular region having a blockage. The catheter member may be made of flexible tubular material that facilitates balloon action, or may be made of ceramic fibers whose structure facilitates transmission of sound impulses to the location to be cleared. The ultrasound generator is a commercially available medical equipment unit adapted to couple to the catheter's central port to deliver the sound impulses. The light source is of the type used in the fluoroscopy field, and is also adapted to couple to the central port of the catheter member. In the preferred embodiment, the catheter member is a five lumen tube in varying lengths depending on the location of insertion site and anatomic location to be obtained, utilizing sound waves to diagnose and treat blockages in the blood vessels, and other organs in the body. The sound waves generated are specific in accordance with a predetermined frequency that will affect each and every atom in a compounds, such as plaque and calcium, comprising a blockage. Every atom in such target compounds has a designated frequency that will cause it to resonate, or "get excited", thus breaking the bonds between atoms and freeing them. In the preferred embodiment, the ultrasonic catheter system comprises a catheter member supported by a portable ultrasound computer allowing visualization of blockages and diagnosis as well as direct treatment using sound bombardment of the site to break up the blockage.

Other features of the present invention are disclosed or apparent in the section entitled: "DETAILED DESCRIPTION OF THE INVENTION."

BRIEF DESCRIPTION OF DRAWINGS

For fuller understanding of the present invention, reference is made to the accompanying drawings wherein.

Figure 1:
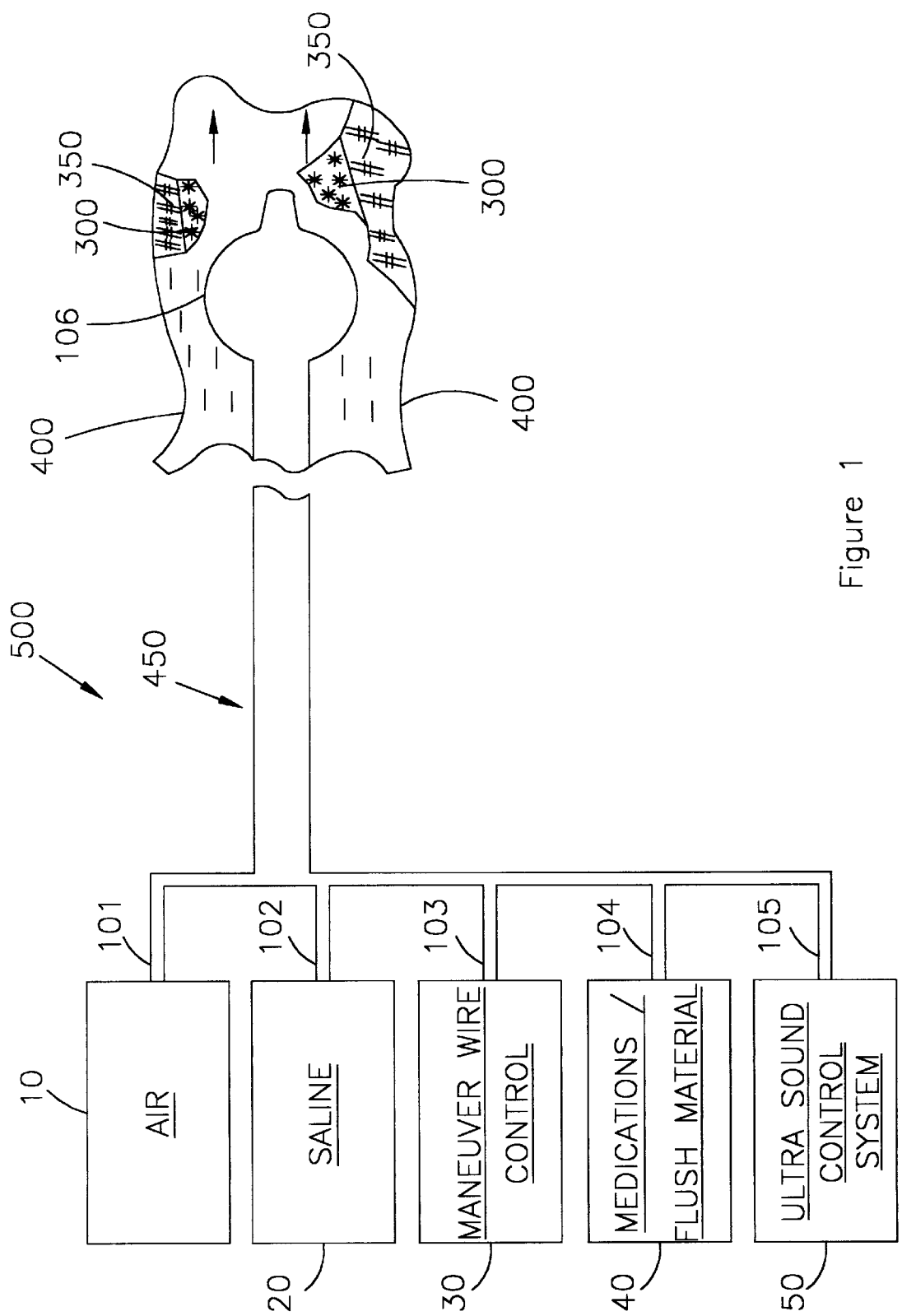
FIG. 1 illustrates a schematic view of the ultrasonic cardiac catheter system of the present invention.

Reference numbers refer to the same or equivalent parts of the present invention throughout the several figures of the drawing.

DETAILED DESCRIPTION OF THE INVENTION

Figures 2, 3:
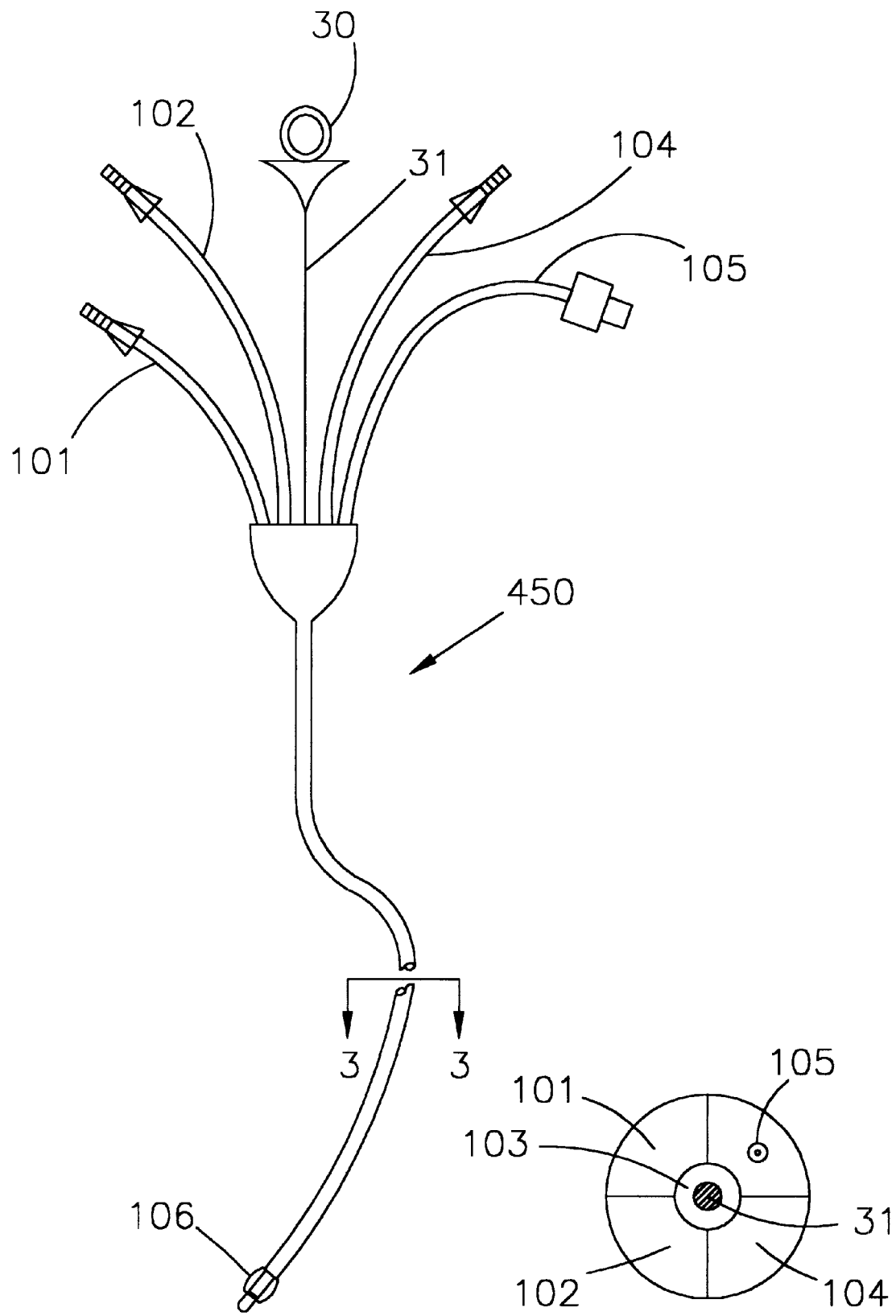
FIG. 2 illustrates the catheter, balloon and ports used in the system illustrated in FIG. 1.
FIG. 3 illustrates a cross-section taken along line 3—3 of FIG. 2, showing the arrangement of the passageways within the catheter.
Figure 4:
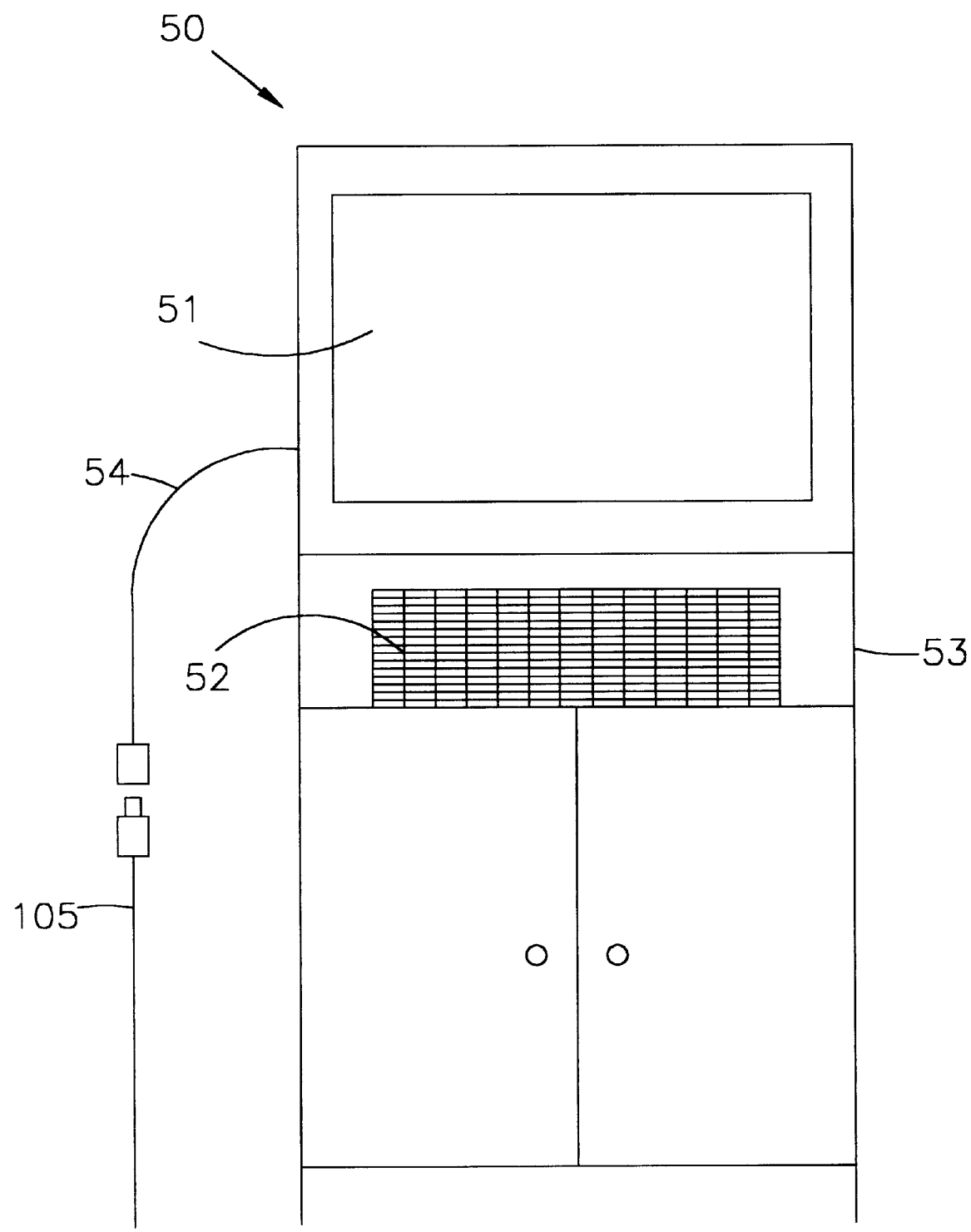
FIG. 4 illustrates an ultrasound controller system that controls the ultrasound and displays the target blockage.

As briefly discussed above, and as shown in FIG. 1, the schematically illustrated catheter system 500 comprises a catheter 450 connected to than air outlet 10, a saline source 20, a maneuver wire control 30, a flush material/medication source 40, and an ultrasound control system 50. The catheter 450, also illustrated in FIG. 2, comprises an air port 101, a saline port 102, a wire port 103, a flush port 104, a sound port 105, and a balloon 106. FIG. 3 illustrates a cross-section taken along line 3—3 of FIG. 2 showing the arrangement of the lumen (passageways) within the catheter 450. Air port 101 connects the catheter 450 to the air outlet 10 at a proximal end of the catheter 450. Air port 101 is a passageway formed by a tube and the lumen 101 in the catheter 450. The air outlet 10 is a one way valve that allows air to escape from the catheter 450, but prevents air from entering the catheter 450. Saline port 102 connects the saline source 20 to the catheter 450 at a proximal end of the catheter 450. The saline port 102 is a passageway formed by a tube and the lumen 102 of the catheter 450. The wire port 103 connects the maneuver wire control 30 to the catheter 450 at the proximal end of the catheter 450. The wire port 103 is a housing, which houses a metal guide wire 31 with the ability to be manipulated to turn the distal end of the catheter into the location to be treated by the thumb and pushing or pulling on the maneuver wire control 30, formed by a loop, to turn left or right as needed. The flush port 104 connects the flush material/medication source 40 to the catheter 450 at the proximal end of the catheter 450. The flush port 104 is formed by a tube and a lumen passing through the catheter 450. The ultrasound port 105 connects the ultrasound control system 50 to the catheter 450 at the proximal end of the catheter 450. The ultrasound port 105 is formed by one or more electrical wires. FIG. 4 illustrates a display 51, data entry system 52, and processor 53 which form the ultrasound control system 50 and which are connected to ultrasound port 105 by a link 54.

Figure 5:
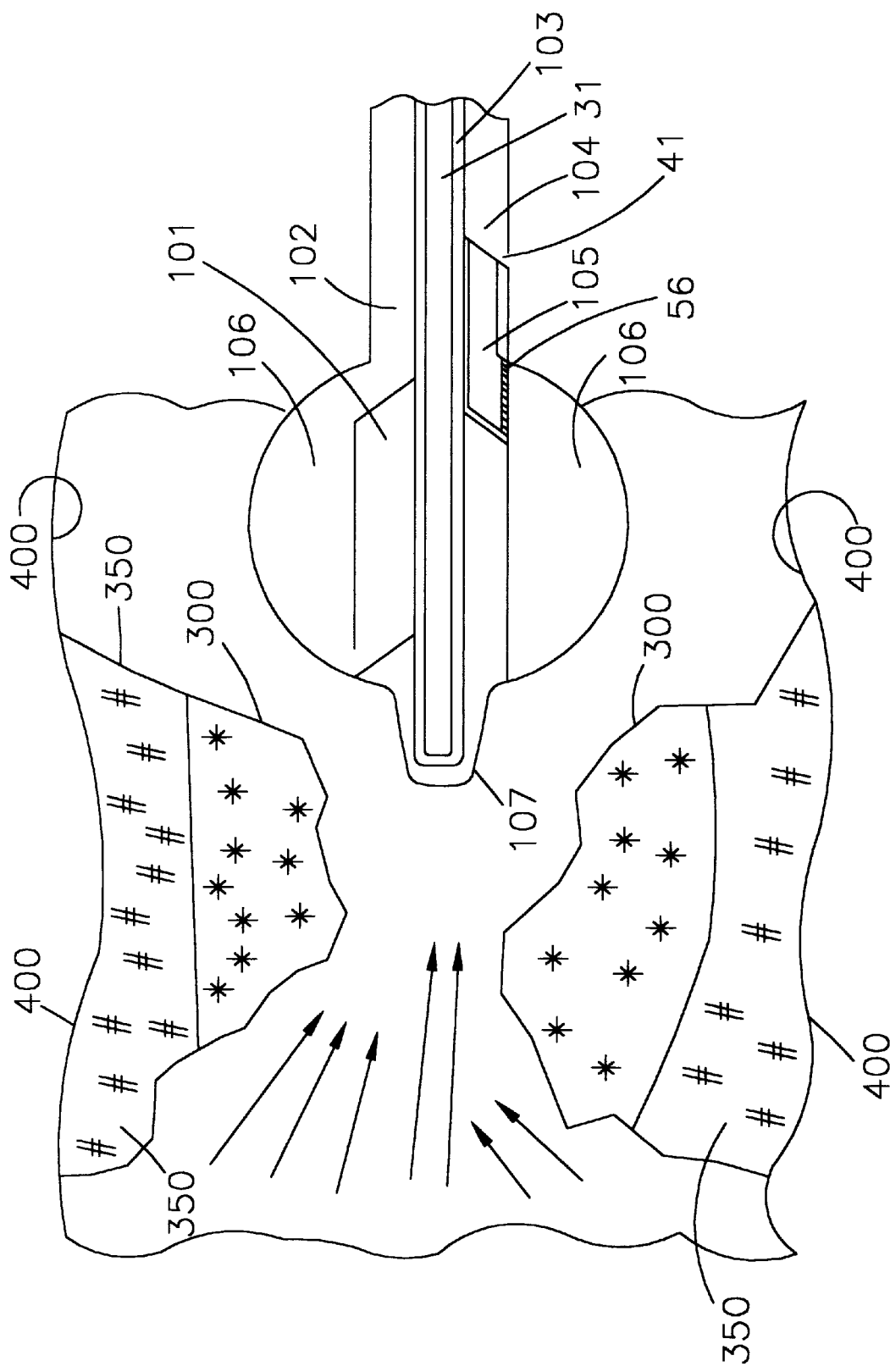
FIG. 5 illustrates an enlarged cross-section of a vessel having a blockage portion and having an ultrasonic catheter apparatus disposed generating ultrasonic waves for emulsifying the blockage with sound waves, in accordance with the present invention.

FIG. 5 illustrates an enlarged cross-section of a vessel 400 in a cardiovascular system and having a blockage portion 300, 350 and having the distal end of the catheter 450 disposed. The balloon 106 is located near the distal end of the catheter 450. A tip 107 is located at the very distal end of the catheter 450 and is thinner and contains the only the guide wire 31 to allow flexibility for easy travel into tight or hard-to-reach areas of the body. The distal end of the lumen forming the saline port 102 passes into the balloon 106 and then into the distal end of the lumen forming the air port 101. The lumen forming the flush port 104 has an opening 41 at the distal end of the flush port 104. The ultrasound port 105 terminates with an ultrasound transducer 56 for passing the ultrasound signal into the balloon 106 and receiving reflected ultrasound signals from the distal end of the catheter 450.

In operation in preparation for insertion, the catheter 450 must be filled with sterile normal saline. With the distal end down saline is pumped into the catheter from the saline source 20 through the saline port 102. Air in the catheter 450 flows upward to the air port 101 where it is extracted via the one way valve in the air outlet 10 thus removing all the air from the catheter 450 and filling the balloon 106 with saline. Ultrasound port 105 is attached by the link 54 to the ultrasound control system 50. The catheter 450 is inserted through the skin of a patient by first locating the appropriate site, and inserting a dilator and a sheath. Insertion of the catheter 450 into the sheath maintains sterility and yet allows for mobility, the catheter 450 is then manipulated into the proper location by pushing the catheter 450 into the patient and using the guide wire 31 to turn the tip 107. Once the catheter 450 is in place, the balloon 106 is then inflated against the blockage.

Figure 6:
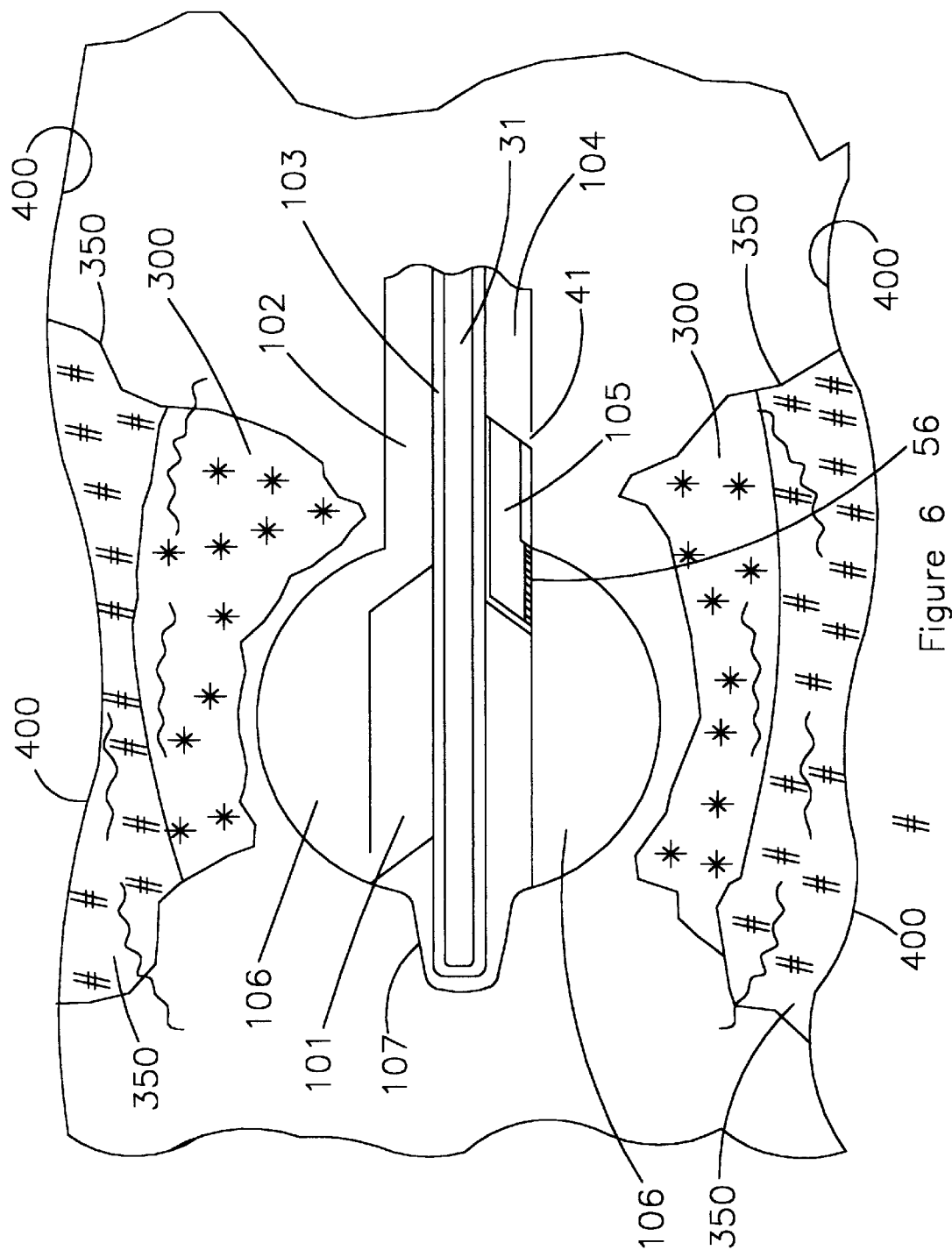
FIG. 6 illustrates an enlarged cross-section of the vessel shown in FIG. 5 showing the ultrasonic wave action for emulsifying the blockage, in accordance with the present invention.
Figure 7:
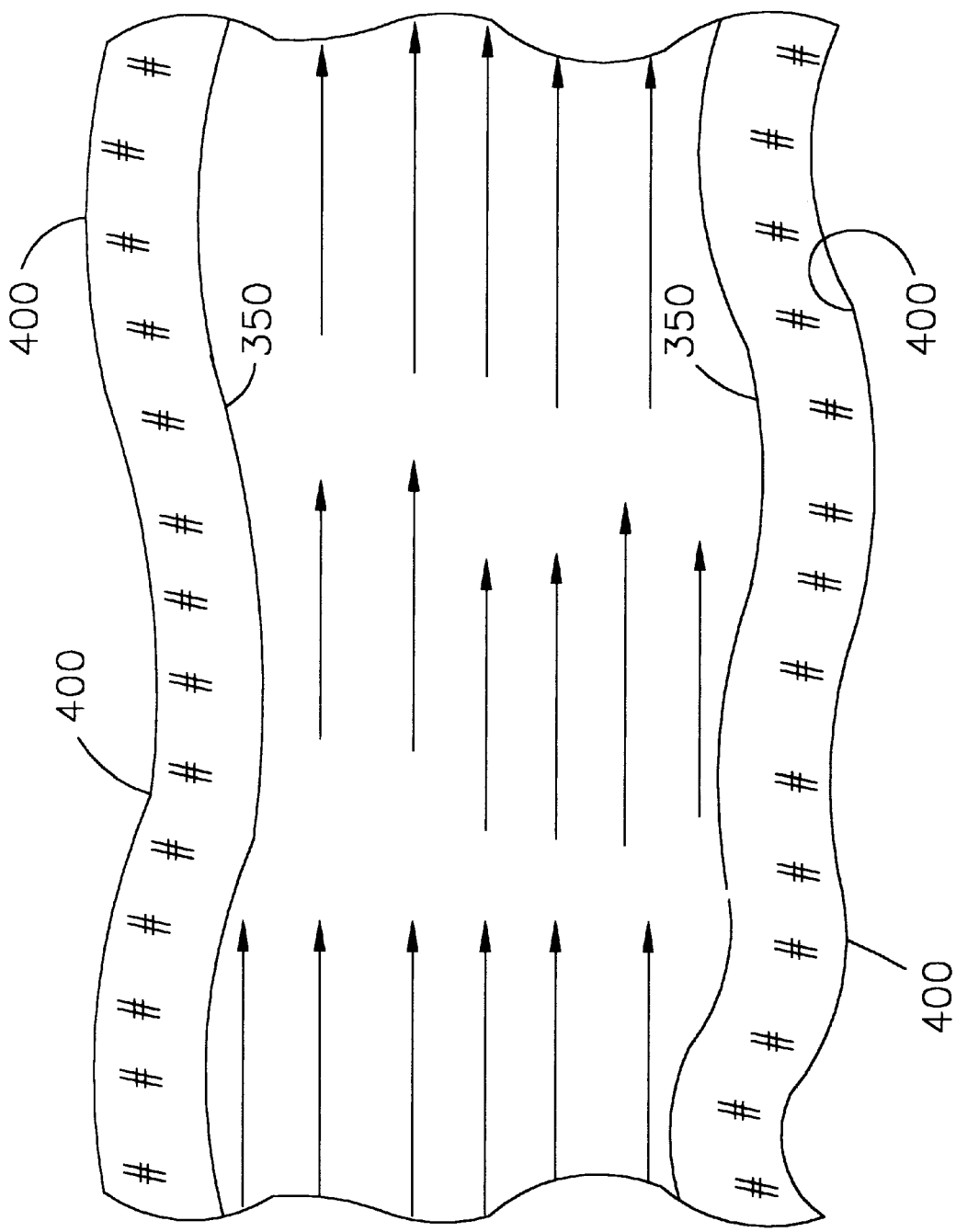
FIG. 7 illustrates an enlarged cross-section of the vessel shown in FIGS. 5 and 6 showing the vessel cleared of the blockage, in accordance with the present invention.

The data entry system 52, which may be a keyboard and mouse, is used to start the processor 53 to signal the ultrasound control system 50 to generate a diagnostic ultrasound signal. The diagnostic ultrasound signal is transmitted through the link 54 to the ultrasound port 105 and then to the ultrasound transducer 56, which transmits diagnostic power ultrasonic bursts through the balloon 106 to the blockage. The diagnostic ultrasonic bursts do not have sufficient power to break the bonds of the blockage, but creates echoes from the blockage. The echoes from the blockage are received by the ultrasonic transducer 56, which sends an echo signal generated by the echo through the ultrasound port 105 and through the link 54, to the ultrasound control system 50. The processor 53 in the ultrasound control system 50 processes the received signal creating an ultrasound image, which is displayed on the display 51 of the ultrasound control system 50. The processor 53 also uses the received signal to determine the density of the blockage and the resonant frequency of the blockage. Processed for density and proper frequency to disrupt the bonds of the blockage, the processor 53 signals the ultrasound control system 51 to generate a treatment ultrasonic burst signal. The treatment ultrasonic burst signal of the resonant frequency calculated by the processor 53 is transmitted through the link 54 to the ultrasound port 105 and then to the ultrasound transducer 56, which transmits treatment power ultrasonic bursts through the balloon 106 to the blockage to break up the blockage (similar to a singer shattering a glass with a note). This can be repeated until the entire blockage is "dissolved" by emulsification. Often a blockage will be caused by materials of different densities. FIG. 5 shows that a first part of the blockage 300 is a material of a first density, and a second part of the blockage 350 is of a material of a second density different from the first density. The processor 53 will first determine the resonant frequency for the first part of the blockage 300, and signal for treatment bursts to liquify the first part of the blockage, as shown in FIG. 6. After transmitting treatment bursts, the processor 53 transmits diagnostic bursts, to image the blockage to see if the first part of the blockage 300 has been removed. If some of the first part of the blockage remains, then the processor 53 transmits treatment bursts for the first part of the blockage 300. If the first part of the blockage 300 has been removed, then the processor 53 transmits treatment bursts that are resonant to the second part of the blockage 350. The processor 53 alternates between diagnostic bursts and treatment bursts, until the diagnostic bursts indicate that the blockage has been reduced to an acceptable level, as shown in FIG. 7. Two main categories of blockage are blockages from Low Density Lipoproteins and blockages from Very Low Density Lipoproteins. There are several subcategories of each of the above categories, having different densities and different resonant frequencies. The different types may form layers upon each other. The ability to measure and determine the resonance frequency of the particular layer of blockage is useful in removing the blockage by ultrasound.

Flush port 104 is used as a flush and/or medication delivery system through the opening 41. This port may be used to administer TPA and other clot-busting agents if needed directly to the area of treatments as needed.

In this specification and claims the use of the inventive catheter in the cardiovascular system is defined as using the catheter in the heart and blood vessels, such as veins and arteries, which also included the use in renal vessels to dissolve kidney stones.

The present invention has been particularly shown and described with respect to certain preferred embodiments and features thereof. However, it should be readily apparent to those of ordinary skill in the art that various changes and modifications in form and detail may be made without departing from the spirit and scope of the inventions as set forth in the appended claims. The inventions illustratively disclosed herein may be practiced without any element which is not specifically disclosed herein.

We claim:

1. An apparatus for removing blockage, comprising:
    a catheter with a distal end for inserting into the cardiovascular system and a proximate end opposite from the distal end; and
    an ultrasound controller electronically connected to the proximate end of the catheter, comprising:
        means for sending diagnostic ultrasonic burst signals to the catheter;
        means for receiving echo signals of the diagnostic ultrasonic burst signals from the catheter;
        means for measuring the blockage from the echo signals; and
        means for generating treatment ultrasonic burst signals, wherein the treatment ultrasonic burst signals are able to generate an ultrasonic burst which is able to break up the blockage.

2. The apparatus, as recited in claim 1, wherein the means for measuring the blockage from the echoes, comprises means for determining whether the blockage is of a first density or a second density.

3. The apparatus, as recited in claim 2, wherein the means for generating treatment of ultrasonic burst signals, comprises means for generating treatment ultrasonic burst signals of a first frequency if blockage of a first density is found and means for generating treatment ultrasonic burst signals of a second frequency if blockage of a second density is found.

4. The apparatus, as recited in claim 3, wherein the catheter comprises:
    a transducer; and
    a ultrasound port extending from the transducer to the ultrasound controller wherein the transducer transmits diagnostic ultrasound burst when the transducer receives a diagnostic burst signal from the ultrasound controller, and wherein the transducer generates an echo signal from echoes received by the transducer, and wherein the transducer transmits treatment ultrasonic bursts of a first frequency when transducer receives treatment ultrasonic burst signals of the first frequency and wherein the transducer transmits treatment ultrasonic bursts of a second frequency when transducer receives treatment ultrasonic burst signals of the second frequency.

5. The apparatus, as recited in claim 4, further comprising a saline source, and wherein the catheter further comprises a saline port connected to the saline source at the proximate end of the catheter and extending through the catheter to the distal end of the catheter.

6. The apparatus, as recited in claim 5, wherein the catheter further comprises a balloon at the distal end of the catheter and in fluid connection with the saline port.

7. The apparatus, as recited in claim 6, wherein the catheter further comprises an air port in fluid connection with the balloon.

8. The apparatus, as recited in claim 7, further comprising an air outlet in fluid connection with a distal end of the air port.

9. The apparatus, as recited in claim 8, further comprising;
    a maneuver wire control; and
    a guide wire connected to the maneuver wire control, wherein the catheter further comprises a wire port surrounding the guide wire and extending from the maneuver wire control at the proximate end of the catheter to the distal end of the catheter.

10. The apparatus, as recited in claim 9, wherein the catheter further comprises a flush port extending from an opening in the proximate end of the catheter to an opening in the distal end of the catheter.

11. A method for removing blockage, comprising the steps of:
    inserting a catheter into a cardiovascular system and adjacent to a blockage;
    transmitting a diagnostic ultrasonic burst from the catheter into the cardiovascular system;
    receiving echoes from the diagnostic ultrasonic burst into the catheter;

analyzing the echoes to measure the blockage; and transmitting a treatment ultrasonic burst from the catheter to dissolve the blockage.

12. The method as recited in claim 11, wherein the step of analyzing comprises the steps of:

determining the density of the blockage; and determining the resonant frequency of the blockage.

13. The method as recited in claim 12, further wherein the step of transmitting a treatment ultrasonic burst, comprises the steps of transmitting a treatment ultrasonic burst of a first frequency if blockage is found at a first density and transmitting a treatment ultrasonic burst of a second frequency not equal to the first frequency if a blockage is found at a second density not equal to the first density.

14. The method as recited in claim 13, further comprising the steps of:

filling a balloon in the catheter with saline solution; and using a guide wire to direct the catheter.

15. The method as recited in claim 14, further comprising the step of introducing and removing fluids from the cardiovascular system through a flush port in the catheter.

16. An apparatus for removing blockage, comprising:

a catheter with a distal end for inserting into the cardiovascular system and a proximate end opposite from the distal end, comprising:

a balloon located at the distal end of the catheter;

an ultrasonic transducer located at the distal end of the catheter;

a saline port extending from the balloon through the catheter to the proximate end of the catheter; and a ultrasound port extending from the ultrasonic transducer through the catheter to the proximate end of the catheter;

a saline source connected to the proximate end of the saline port; and an ultrasound controller connected to the proximate end of the ultrasound port, wherein the ultrasound controller comprises:

a display;

a data entry system; and a processor connected between the display, data entry system, and ultrasound port, wherein the processor comprises:

means for determining the density of the blockage; and means for determining the resonant frequency of the blockage; and means for generating a signal, which causes the ultrasonic transducer to generate an ultrasonic burst at the resonant frequency of the blockage.

\* \* \* \* \*